United States Patent [19]

Adda et al.

[11] Patent Number: 5,306,828
[45] Date of Patent: Apr. 26, 1994

[54] PROCESS FOR THE MANUFACTURE OF SUBSTITUTED MALEIMIDES

[75] Inventors: Michel Adda, Haifa; Chaim Eidelman, HaGalil; Leonard Shorr, Haifa, all of Israel

[73] Assignee: Bromine Compounds Ltd., Beer-Sheva, Israel

[21] Appl. No.: 835,198

[22] Filed: Feb. 13, 1992

[51] Int. Cl.$^5$ ............... C07D 207/44; C07D 207/452; C07D 401/04
[52] U.S. Cl. .................... 548/548; 548/549; 548/522; 546/175
[58] Field of Search ............... 548/548, 522, 549; 546/175

[56] References Cited

U.S. PATENT DOCUMENTS

| | | | |
|---|---|---|---|
| 2,444,536 | 7/1948 | Searle et al. | 548/548 |
| 3,496,191 | 2/1970 | Cahoy et al. | 548/548 |
| 3,758,498 | 9/1973 | Pfuller et al. | 548/548 |
| 4,780,546 | 10/1988 | Kita et al. | 548/548 |

FOREIGN PATENT DOCUMENTS

| | | | |
|---|---|---|---|
| 1934791 | 1/1971 | Fed. Rep. of Germany | 548/548 |
| 0120502 | 7/1982 | Japan | 548/548 |
| 60-109562 | 6/1985 | Japan | |
| 2252763 | 11/1987 | Japan | 548/522 |

OTHER PUBLICATIONS

Patent Abstracts of Japan 10(136) (C-347) (2193) May 20, 1986.
Patent Abstracts of Japan 10(287) (C-375) (2343) Sep. 30, 1986.
Patent Abstracts of Japan 11(75) (C-408) (2522) Mar. 6, 1987.
Patent Abstracts of Japan 9(254) (C-308) (1977) Oct. 11, 1985.

*Primary Examiner*—David B. Springer
*Attorney, Agent, or Firm*—Michael N. Meller

[57] ABSTRACT

In a process for the preparation of substituted maleimides the corresponding amines are reacted with maleic anhydride and the thermal imidization of the resulting substituted amic-acids is effected in a mixed apolar/polar aprotic solvent medium in the presence of an acid catalyst, a substantial portion of the apolar solvent is subsequently selectively removed from the reaction mixture and most of the final product is precipitated.

24 Claims, 6 Drawing Sheets

PROCESS FOR THE MANUFACTURE OF SUBSTITUTED MALEIMIDES

FIELD OF THE INVENTION

The present application relates to a process for the preparation of substituted maleimides. Of particular interest is the preparation of bis-maleimides.

BACKGROUND OF THE INVENTION

Maleimides and polyimides have become important components in the plastics industry. Their application as plastics additives and in high performance composites enhances thermal and chemical stability, resistance to wear and impact, and ease of workability. Thus, the addition of 5%-10% N-phenylmaleimide (PMI) to ABS plastics increases their heat distortion temperatures to over 125° C. Bismaleimides (BMI), such as 4,4'-bis-maleimido-diphenylmethane (MDA-BMI), are monomers used in the production of high performance polyimide resins for application in structural materials in the aviation, electrical, electronics and aerospace industries. The improved properties they provide could benefit a wider range of applications which seek better performance from lighter weight materials. However, their high cost limits such opportunities.

Their high production cost is largely a result of the low yields of high purity product obtained, the complex operations involved and waste treatment, costs involved in the industrial processes used until now for the monomer manufacture. Their synthesis, by the condensation of amines with maleic anhydride in two successive steps (formation of amic-acids and imidization thereof, which, in the case of this invention, is performed by a thermal route), is deceptively simple. Yet, as reported by Breitigam and Stenzenberger (Soc. of Plas. Eng., Conf. on High Temperature Polymers, Oct. 2–4, 1989), the yields of polymer grade monomers of this family obtained are usually in the range of only 65%–75%. Isoimides, anilides, fumaramic acid derivatives and oligomeric by-products are obtained, among other impurities. In the case of BMI, any misdirected reaction with one of the amino groups is doubly felt, for it automatically renders the other amino-functionality unproductive as well. Not only are raw materials costs relevant to the process economics, but the manufacturing operations involved in complex purification steps, solvent recovery as well as difficult waste disposal problems, in some cases, of toxic materials, such as MDA, add to the manufacturing expense. For example, in the latter instance, MDA concentrations in the MDA-BMI product in the ppm range are required. Equally stringent restrictions are placed on the concentration of MDA in waste effluent. OSHA (Occupational Safety and Health Administration) suggests a 10 ppb exposure limit (100 ppb short term exposure) for this compound (Chemical Regulation Reporter, 0148-7973/89, May 19, 1989, page 197).

The thermal imidization of the amic-acids is acid catalyzed and is performed in an inert liquid medium, from which the water of condensation is removed by azeotropic distillation. The basic concept of this process is described in U.S. Pat. No. 2,462,835. However, the high temperatures required lead to unwanted isomerizations, condesations and polymerizations.

When the inert medium is a hydrocarbon or halocarbon, the insolubility of both the amic-acids and the maleimides leads to the precipitation of contaminated product. It has been reported (e.g. in JP 85,260,623; JP 86,106,554; JP 86,229,863; JP 236763/86; JP 159764/82) that the use of an apolar solvent in conjunction with an aprotic polar solvent leads to improved results. However, the reaction conditions applied, the methods used for product isolation and the quality of the maleimides produced are not satisfactory. For example, in JP 615976/82, using ethylene dichloride (EDC) and dimethylformamide (DMF) as the mixed solvent to produce MDA-BMI, the reaction time was 20 hours and the product was only 93% pure.

In JP 236763/86, the same material was produced in a mixture of toluene and DMF. Great care was exercised to control the distillation at a precise rate over a period of 15 hours. Yet the product purity was only 96%. Furthermore, it was recovered from the reaction mixture by distilling both solvents under reduced pressure and adding the remaining concentrate dropwise to an aqueous sodium carbonate solution. Both the p-toluenesulfonic acid (PTS) (used as a catalyst) and the DMF contained in the concentrate, dissolve in water and cannot be recovered in a practical way; this in addition to the ecological problem presented. This process is clearly inapplicable on an industrial scale.

JP 229863/86 describes a very similar process with the same unsatisfactory results.

JP 260,623/60 performed the dehydration for a shorter period of time and recovered the product by dropping the (sometimes concentrated) reaction mixture into water or by precipitation with excess methanol. Product of similar purity was obtained, but no practical solution is offered for the recovery of materials used. Neither is there any reference to the residual MDA level.

It should be noted that in all of these cited patents, amic-acid production is effected in the same mixed solvent mixture (but catalyst free) as that used in the second, imidization step. The importance of this feature will be seen below.

SUMMARY OF THE INVENTION

It has now been found that in the thermal imidization process (using mixed apolar/polar aprotic solvents), when a substantial, preferably a major portion of the apolar solvent is selectively removed from maleimide reaction mixtures, the maleimides preferentially precipitate out in a high state of purity. Simply by washing, products of commercially acceptable purity are obtained. Accordingly, the process according to the invention comprises the preparation of maleimides by reaction of maleic anhydride with the corresponding amines and subsequent thermal imidization in a mixture of at least an apolar and at least a polar aprotic solvent, characterized in that a substantial, preferably a major part of the apolar solvent is subsequently selectively removed from the reaction mixture.

The fraction of apolar solvent which is removed in the product precipitation stage influences the extent and purity of the product which precipitates. It is a function of the solvent pair used in the process, the solubility characteristics of the maleimide and the temperature which is convenient for filtration. Generally, substantially 50%–90% of this component of the mixed solvent is selectively distilled out, preferably 60%–80%.

Not all of the product maleimide precipitates in this selective (with respect to the solvent which is removed) concentration step. The remainder of that formed is retained in the mother liquor, along with reaction intermediates, unreacted maleimide anhydride, catalyst and the impurities. It is to be noted that maleic anhydride is preferably used in excess, in the amic-acid formation step, both to guarantee efficient reaction and to ensure complete conversion of the amine.

It is of course desirable, and in some cases, of economic necessity, to recover all of the reagents, product and catalyst. This cannot be done directly because of the (sometimes oligomeric) impurities also contained in the mother liquor. However, it has been found, and this is an additional surprising feature, that if the mother liquor is rediluted with the apolar solvent, the impurities precipitate preferentially, as a separate phase which can be easily removed leaving a purified mixture which can be recycled.

Accordingly, a preferred embodiment of the invention is characterized in that, after the aforesaid selective removal of a major portion of the aprotic solvent from the reaction mixture and the separation of the precipitated maleimide, the mother liquor remaining is rediluted with the said apolar solvent, and preferably the precipitated impurities are removed and the purified mother liquor is recycled.

The amount of apolar solvent used in diluting the mother liquor depends on the nature of each of the two solvents used, the amount of apolar solvent selectively removed from the reaction mixture to precipitate the product, the solubility properties of the substituted maleimide, the amount and nature of the impurities formed and the temperature chosen for the mother liquor dilution. Very generally, a volume fraction of 0.5–1.5 of the original is used for redilution and preferably 0.7–1.3.

The imidization process does not proceed well if the treated mother liquor is recycled to the stage of amic-acid formation. Fortunately, no such interference is encountered when it is recycled to the imidization stage. Some of the apolar solvent removed in the product precipitation stage can be used for amic-acid production.

The preferential precipitation of the oligomeric impurities by the partial reconstitution of the original solvent mixture, is exactly the reverse of that which would be expected, since from this same solvent mixture it was previously the product which precipitated selectively, leaving the impurities behind. It is not clear why this reverse behavior occurs. It may be due to the retention of impurities in the original reaction mixture by the product maleimide, which, once removed, no longer serves to solubilize the impurities. It may also be due to chemical changes which take place in the system during the concentration step.

DETAILED DESCRIPTION OF PREFERRED EMBODIMENTS

Figure 1:
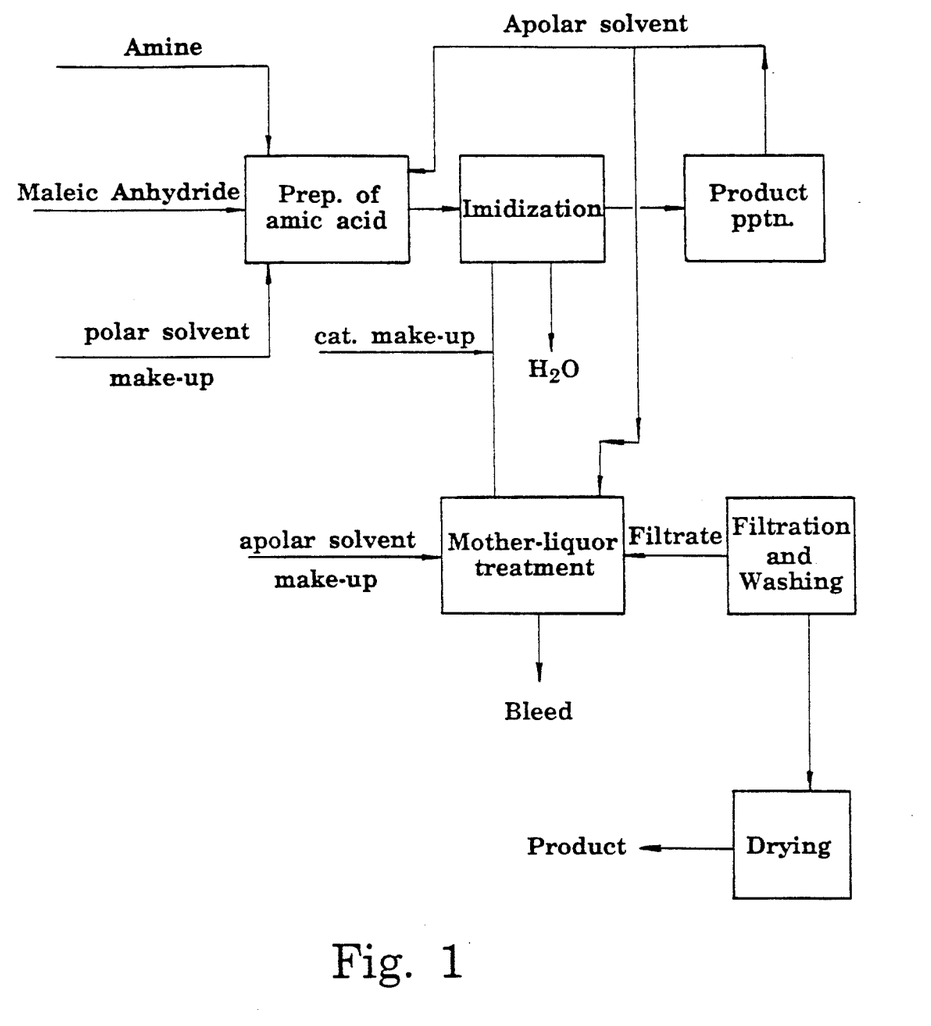
FIG. 1 is a flow diagram of a preferred embodiment of the process according to the invention.

The process according to the invention will be better understood with reference to the flow diagram of FIG. 1.

The amine, corresponding to the desired maleimide, is reacted with excess maleic anhydride (up to 60% excess and preferably 5–10% excess) in a mixture of the apolar/polar solvents and in the absence of a catalyst at a temperature of 40°–100° C. (preferably 50°–80° C.) to form the amic-acid. To this mixture, mother liquor (treated as described below) is then added along with make-up catalyst and solvents, as required. Thermal imidization is then conducted at 50°–150° C. (preferably 90°–120° C.) in a reactor equipped with distillation equipment capable of separating the polar from the apolar solvent. The water formed in the reaction is removed by distillation. When aqueous distillate ceases, the major part of the apolar solvent is distilled out. The concentrate is then cooled. The product precipitates. It is filtered out, washed and dried.

For oxidation-sensitive amines, it may be desirable to perform these reactions in an inert atmosphere, such as is provided by nitrogen.

Amic-acids prepared in any other manner can be readily treated in the imidization stage of the process according to the invention.

It is sometimes desirable to filter the reaction solution prior to its concentration to remove insoluble material which may be present at that stage.

The mother liquor is then treated by redilution with part of the stripped apolar solvent. The small amount of oligomeric impurities separates as a discrete phase and is discarded, while the second phase, which contains some of the product, catalyst and incompletely converted reagents is recycled to the imidization stage.

The reaction duration is a function of the amine used, the reaction temperature, and the volume and composition of the solvent system. Nevertheless, amic-acid formation is performed over a period of 0.1–10 hours (preferably 0.25–1.0 hour) and the imidization usually is carried out over a period of 0.5–72 hours (preferably 1–4 hours).

The amount and choice of solvents used are primarily determined by the nature of the amine and that of the product obtained. It is usually desirable to select these so that complete dissolution has occurred when all of the water of the reaction has been removed. But it is enough to use a minimum of solvent, sufficient to allow for adequate mixing. It is a requirement that the apolar solvent boils sufficiently below the polar solvent so that it can be readily separated therefrom without requiring equipment of excessive distillation efficiency. If the boiling point of either or both of the solvent components is so high that the boiling point of the reaction mixture at normal pressures is above 150° C., or undesirably high temperatures are reached during the concentration step, vacuum can be applied in either or both of these steps so as to avoid the application of excessive heat.

Nevertheless, the amount of solvent used varies from 1.5–20 parts for each part of maleimide produced (preferably 2–9 parts per part of maleimide). The ratio of apolar to polar solvent is normally 99%–10% of the former to 1%–90% of the latter (preferably 5%–20%, and most preferably 10%–15%, of the mixture being polar solvent).

The process according to the invention can be carried out in batch, semi-batch or continuous operation. It is preferred to carry it out continuously.

Examples of amines that can be used in the method of the present invention are: m-phenylenediamine, aniline, toluidine, p-phenylenediamine, 4,4'-diaminodicyclohexylmethane, 1,4-diaminocyclohexane, 2,6-diaminopyridine, 4,4'-diaminodiphenylmethane, 2,2-bis (4- aminophenyl) propane, 4,4'-diaminodiphenyl ether, 4,4'-diamino-3-methyldiphenyl ether, 4,4'-diaminodiphenylsulfide, 4,4'-diaminobenzophenone, 4,4'-diaminodiphenylsulfone, bis (4-aminophenyl) phenylamine, m-xylylenediamine, p-xylylenediamine, cyclohexylamine, 3-methyl-4,4'-diaminodiphenylmethane, 3,3'-diethyl-4,4'-diaminodiphenylmethane, 3,3'-dichloro-4,4'-diaminodiphenylmethane, 2,2',5,5'-tetrachloro-4,4'-diaminodiphenylmethane, 2,2-bis (3-methyl-4-aminophenyl) propane, 2,2-bis (3-ethyl-4-aminophenyl) propane, 2,2-bis (2,3-dichloro-4-aminophenyl) propane, bis (2,3-dimethyl-4-aminophenyl) phenylethane, ethylenediamine, hexamethylenediamine, xylidines, and the like.

Examples of apolar solvents are: pure or mixed benzene, toluene, xylenes, ethylbenzene, diethylbenzene, octanes, methylcyclohexane, butylbenzenes, cumene, mesitylene, halogenated hydrocarbons including chlorobenzene, dichlorobenzenes, o-chlorotoluene, n-chlorotoluene, p-chlorotoluene, 1,2-dichloroethane, 1,2-dichloropropane, carbon tetrachloride, 1,1,1-trichloroethane, 1,1,2-trichloroethane, 1,1,1,2-tetrachloroethane, 1,1,2,2-tetrachloroethane, trichloroethylene, and tetrachloroethylene.

Examples of aprotic polar solvents are: dimethyl sulfoxide, N,N-dimethylformamide, N,N-dimethylacetamide, hexamethylphosphoramide, N-methyl-2-pyrrolidone, etc.

As the acid catalyst, one or more of the following can be used: trifluoroacetic acid, organic sulfonic acids such as benzene sulfonic acid, p-toluenesulfonic acid (PTS), dodecylbenzene sulfonic acids, trifluoromethanesulfonic acid, sulfuric acid, sulfonated polymers such as sulfonated polystyrene and fluoro-polymers, phosphoric acid, polyphosphoric acid, organo-phosphoric acids such as mono- and diethylphosphoric acids, and acidic salts such as sodium or ammonium hydrogensulfate, etc. The acid catalyst is used in an amount of from 0.001 to 1 mole, and preferably from 0.1 to 0.4 mole per mole of the amine. This comprises catalyst recycled with the ML, which is the major part, e.g. about 90%, and make-up catalyst.

In the case of some amines, there is a tendency for the reactants to agglomerate. This poor dispersion leads to the subsequent formation of large amounts of oligomeric by-products. This phenomenon is not unique to the process of the present invention, but is true for processes of the prior art, as well. It has been found, surprisingly, that in these cases coagulation can be prevented and good dispersion achieved by the use of a long chain alkyl benzene sulfonic acid, such as dodecylbenzene sulfonic acid, alone or in combination with another (or others) of the acid catalysts listed above.

The invention will be further illustrated by the following non-limitative examples.

EXAMPLE 1A

Preparation of N-Phenylmaleimide (PMI)-First Cycle

Reaction components:

| | |
|---|---|
| Aniline | 149 g, 1.6 moles |
| MA | 173 g, 1.8 moles |
| DMF | 43 ml |
| Toluene | 2.4 L |
| PTS | 25 g |

A solution of the aniline in 200 ml of the toluene was added over 20 minutes to a vigorously stirred solution of the MA in the DMF and the remaining toluene. The temperature was allowed to rise during this addition from ambient to 60° C. The mixture was heated to 70° C. and stirred for an additional half hour.

Figure 2:
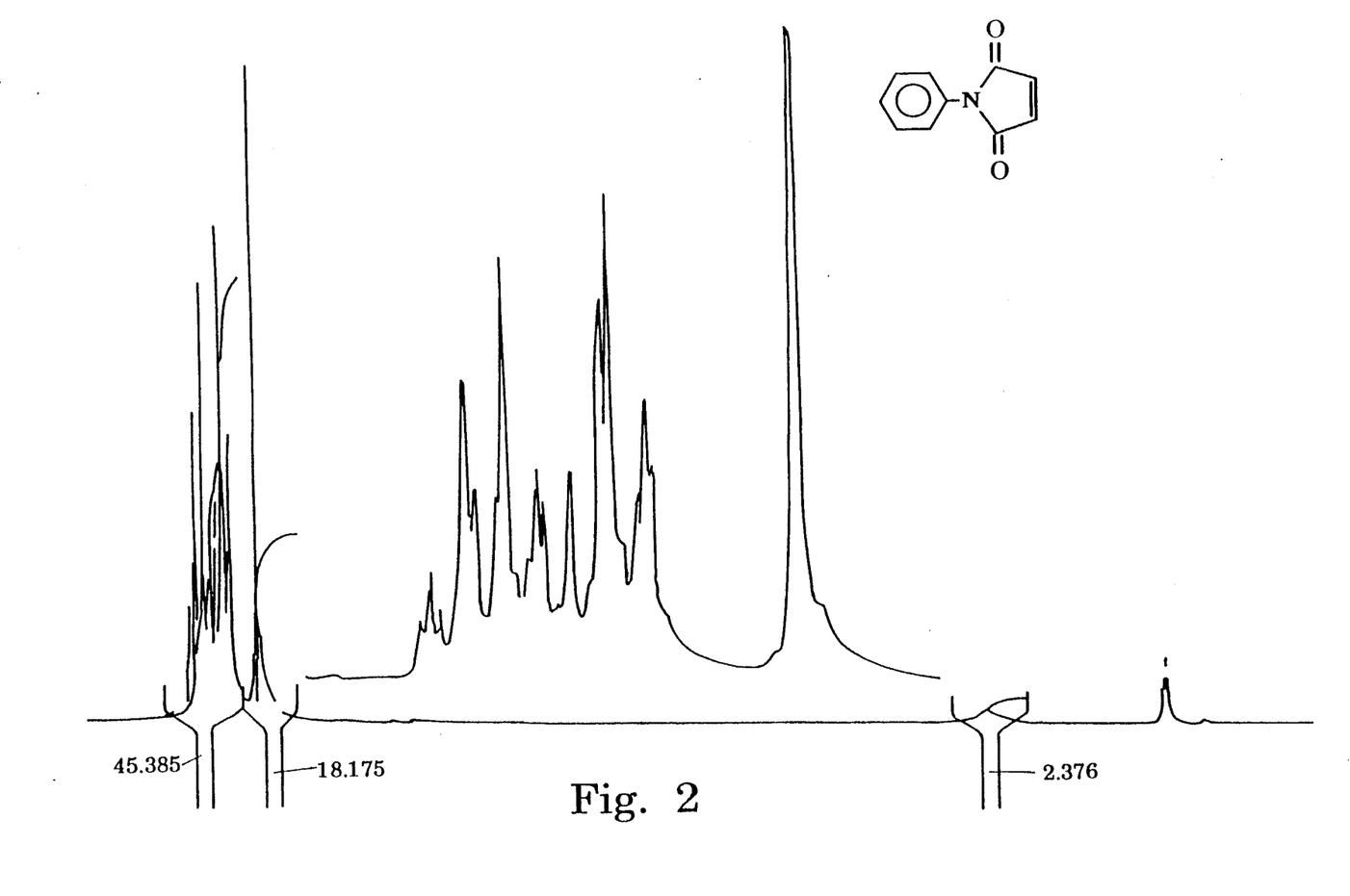
FIGS. 2 to 6 are NMR spectra of maleimides prepared by the process of the invention.

The PTS was added and the temperature raised to 100° C. Vacuum was applied and the mixture stirred at that temperature for two hours while 28 ml of the water distilled over (separated in a Dean-Stark trap). The reaction mixture was concentrated by removing 2 L of toluene through a Vigreux column, then cooled in ice water and filtered. PMI (165 g, 0.94 moles) was recovered in a 60% yield. Its m.p. was 88.5°-89.7° C. and it was found, by DSC analysis, to be 99.7% pure. The NMR spectrum of this product is shown in FIG. 2.

The mother liquor (ML) was diluted with 400 ml of toluene. A small amount of precipitate separated and was discarded. The toluene layer was set aside for recycling to the next batch.

EXAMPLE 1B

Preparation of N-Phenylmaleimide (PMI)—Recycling Procedure

A solution of 149 g aniline in 400 ml toluene, recovered from the concentration step of a previous run was added over a period of 15-20 minutes to a vigorously stirred mixture of 173 g MA in 1600 ml of recovered toluene and 5 ml of DMF. The temperature was kept at 30°-70° C. Stirring was continued at 70° C. for an additional 45 minutes.

The temperature was raised to 100° C. and approximately 500 g of hot (70° C.) treated ML from the previous run was introduced in addition to 2.5 g PTS (10% make-up). The temperature was increased to reflux (105° C. under reduced pressure). Water (ca. 29 ml) evolved in 2 hours. The reaction mixture was filtered and concentrated by the selective distillation of 2 L of toluene. The crystallized product was filtered, washed and dried. PMI was obtained in a 96% yield. Its m.p. was 89°-90° C. and it assayed 99.5% by DSC.

The ML was treated as in Example 1A and stored for the next run.

EXAMPLE 2A

Preparation of MDA-BMI

A solution of MDA (198 g, 1 mole) in DMF (215 ml) was added over a period of 20 minutes to a vigorously stirred solution of MA (215 g, 2.2 moles) in toluene (3 L). The temperature during the operation rose from 30° C. to 70° C. The resulting slurry of the bis-maleamic acid which formed was stirred for an additional 45 minutes at 70° C.

PTS mono-hydrate (31 g) was introduced and the temperature was raised to 90°-105° C. under reduced pressure. The water which formed was removed by azeotropic distillation in a Dean-Stark trap. The end of the reaction (3 hours duration) was determined by the recovery of 36 ml of water and complete dissolution of the reactants in the reaction medium.

The solution was then concentrated by distilling off 2 L of the toluene through a Vigreux column. The concentrate was cooled to product crystallization. The resultant slurry was filtered, washed and dried to obtain 250 g of MDA-BMI (70% yield) of m.p. 154°-189° C. and HPLC assay of >98%.

The ML was diluted by an equal volume of toluene, whereupon a small amount of an oily second layer separated. The oily layer was extracted twice with toluene and discarded. The combined toluene layers were used in a subsequent batch.

Figure 3:
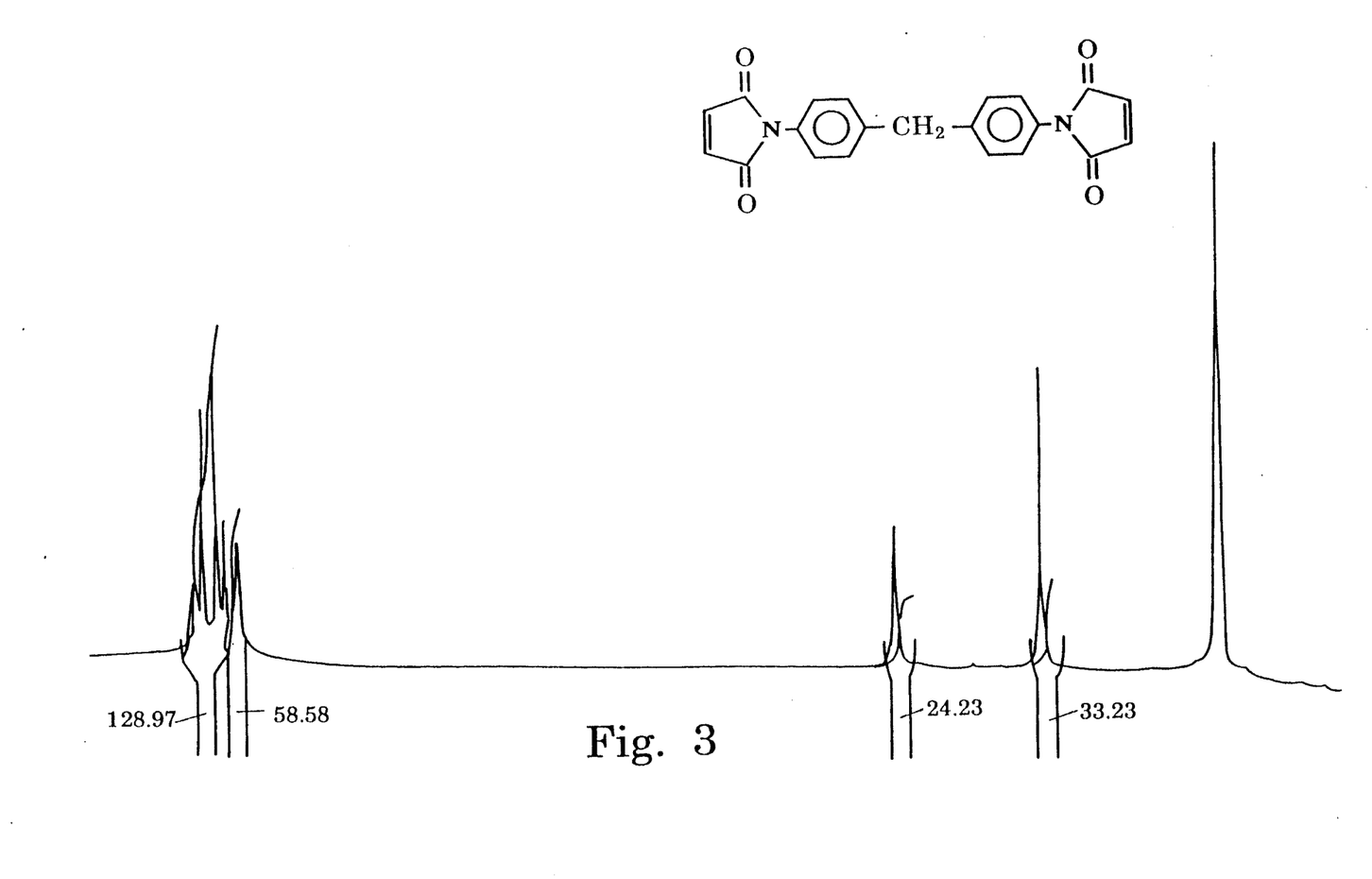

The NMR of this product is given in FIG. 3. By GC-MS, coupled with the method of successive dilutions, it was shown to contain less than the 1 ppm detection limit for MDA, if MDA was present at all.

EXAMPLE 2B

Preparation of MDA-BMI-Recycling Procedure

A hot (60°–70° C.) solution of MDA (139 g, 0.7 mole) in 300 ml of recovered toluene was added over 15–20 minutes to a vigorously stirred solution of MA (144 g, 1.5 moles) in 250 ml of the same recovered toluene and 55 ml of DMF. The temperature rose from 30°–70° C. Stirring was continued at 70° C. for an additional 45 minutes. The temperature was raised to 100° C. and hot (70° C.) treated ML (760 ml) from a previous run (the fourth recycle) was introduced in addition to PTS (13 g) make-up. The temperature was increased to reflux 105° C. under reduced pressure. About 25 ml of water separated in the distillate trap in 4–5 hours.

The reaction mixture was concentrated by distilling out 900 ml of toluene through a Vigreux column. On forced cooling, the crystalline product precipitated. This was filtered out, washed and dried to obtain 236 g, 0.66 mole (94% yield based on the MDA added in this cycle). The quality of this product was as good as that of the previous example.

The ML was treated as in Example 2A and stored for the next run. The total amount of oily material which separated from the MLs of these four runs corresponded to only 5–10% of the product on a weight basis, but contained some of the DMF and PTS.

EXAMPLES 3–9

Preparation of MDA-BMI under various non-optimized conditions

MDA-BMI was prepared from 0.04 mole MDA and 20%–50% excess MA as described in Example 2, but using various polar and apolar solvents and other acid catalysts. In the concentration step of these examples (3–9), the apolar solvent was removed (from 60–80% in each run) by distillation through a Vigreux column under reduced pressure until the solution became cloudy. ML treatment was accomplished by redilution with 0.5–1.5 volumes of the stripped apolar solvent. Other details describing these examples are listed in Table I.

EXAMPLE 10

Preparation of DADPE-BMI

Reagents:

| | |
|---|---|
| 4,4'-Diaminodiphenyl ether | 8.0 g, 0.04 mole |
| MA | 8.6 g, 0.088 mole |
| DMF | 8.6 ml |
| Toluene | 120 ml |
| PTS | 1.24 g |

Figure 4:
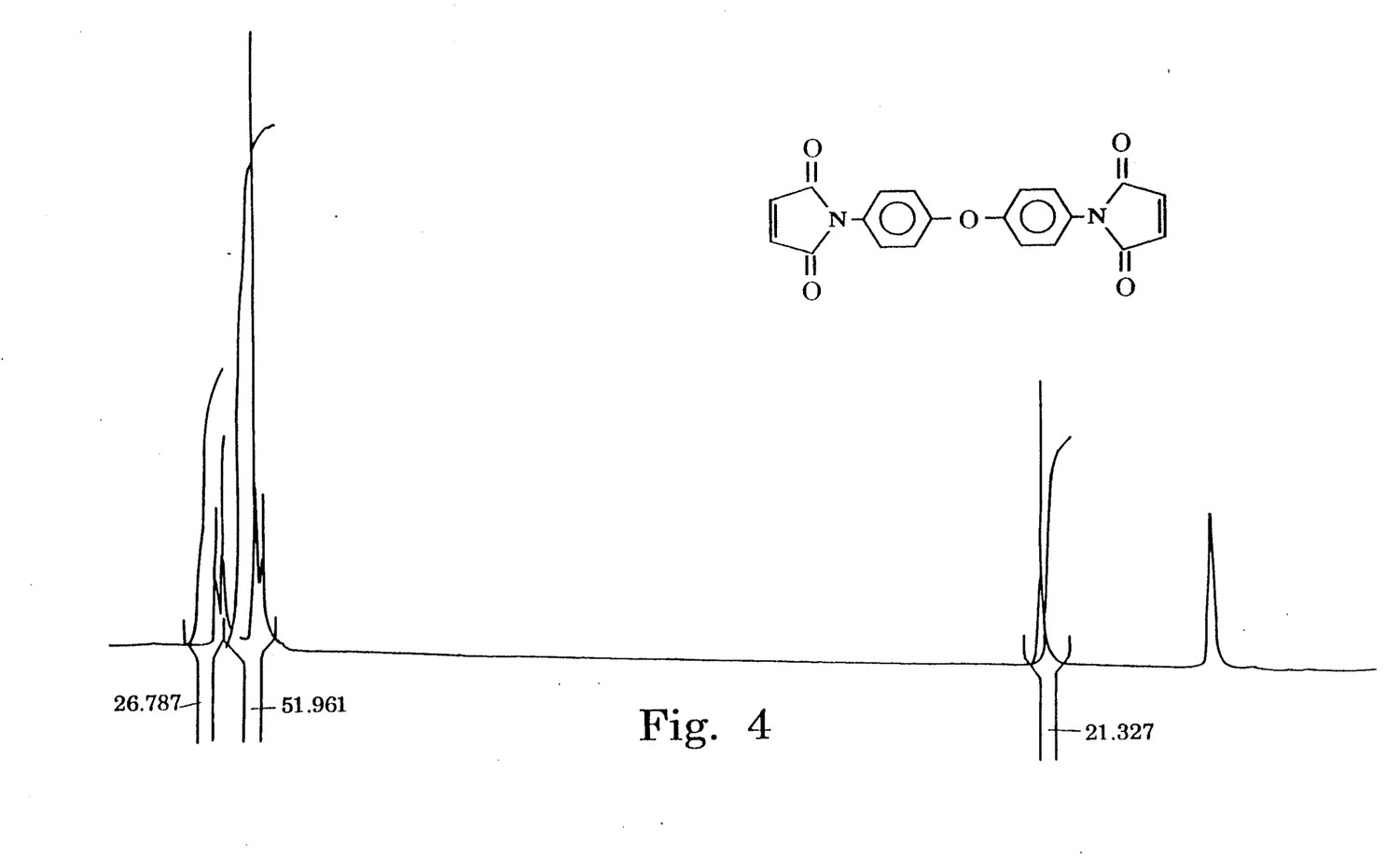

The reaction procedure was similar to that of Example 2. Cyclization was completed within 6 hours. On the first cycle, 11.5 g of the bismaleimide was obtained, in a yield of 80%, which increased on subsequent recycle operations; the average amount of toluene insoluble residue obtained on redilution of the ML amounted to 0.03–0.1 g per g of DADPE-BMI produced. The NMR of a typical product is given in FIG. 4.

EXAMPLE 11

Preparation of PPDA-BMI

Reagents:

| | |
|---|---|
| p-Phenylenediamine | 4.3 g, 0.04 mole |
| MA | 8.6 g, 0.088 mole |
| DMF | 8.6 ml |
| Toluene | 120 ml |
| PTS | 1.24 g |

Figure 5:
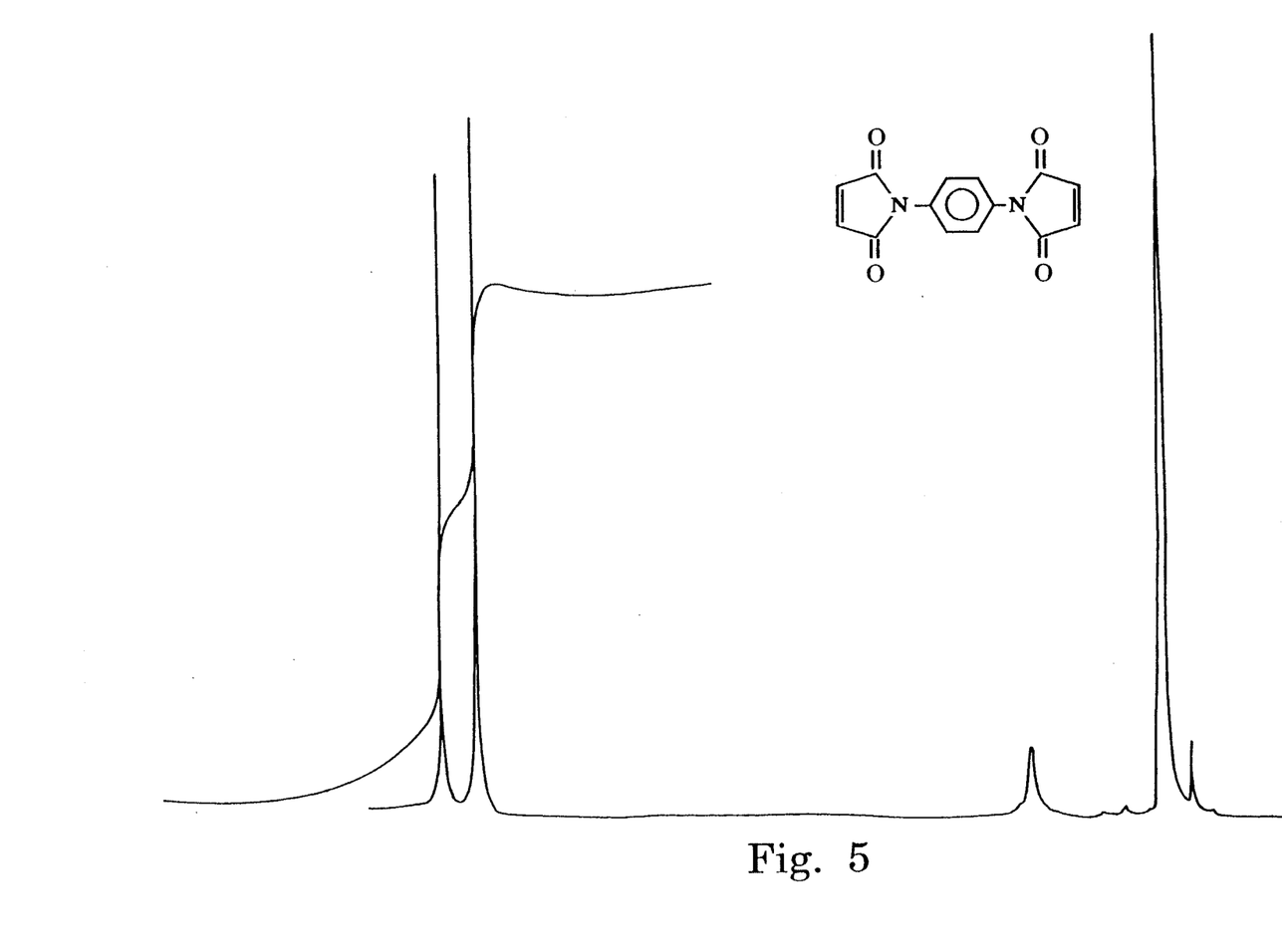

The operating conditions and results were similar to those of the previous Example. The NMR spectrum of a typical product is given in FIG. 5.

EXAMPLE 12

Preparation of 3-Me-4,4'-DADPE-BMI

Reagents:

| | |
|---|---|
| 3-Methyl-4,4'-diaminodiphenyl ether | 86 g, 0.4 mole |
| MA | 86 g, 0.88 mole |
| DMF | 86 ml |
| Toluene | 1200 ml |
| PTS | 12.4 g |

Figure 6:
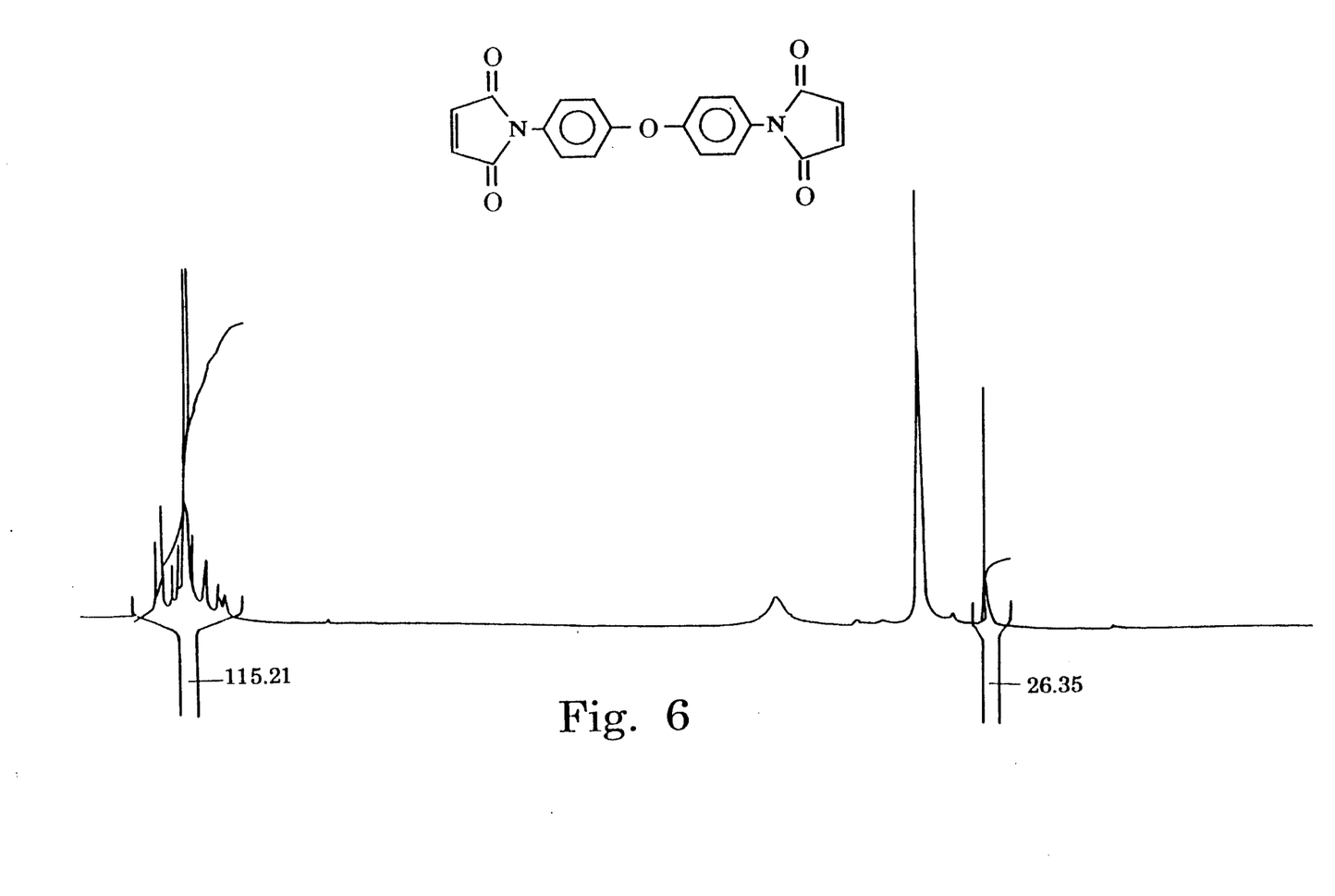

The reaction procedure was similar to that presented in Example 2. Cyclization was complete within 2 hours. The bismaleimide was isolated in the first cycle in a 61% yield (91 g), which increased in recycle runs to an average of 90–95% of pure product. An average make-up amount of 10% of the catalyst was used. A typical NMR spectrum is given in FIG. 6. The m.p. range of products obtained was 154.4°–160.2° C. The average

TABLE I

| | Solvent | | | | Yield (First Cycle) % | | m.p. Range °C. |
|---|---|---|---|---|---|---|---|
| Exp | Polar ml | Apolar 120 ml | Catalyst g | Imidization (h) | | Range | |
| 3 | NMP, 8.6 | Xylene | MeSO$_3$H, 0.63 | 1.5 | 70 | 85–96 | 152–8 |
| 4 | DMAc, 16 | Xylene | Amberlist-15, 15 | 4 | 85 | 95–98 | 155–7 |
| 5 | DMF, 8.6 | Toluene | NaHSO$_4$, 1.5 | 3 | 50 | 80–90 | 153–6 |
| 6 | DMF, 8.6 | Toluene | H$_2$SO$_4$, 0.5 | 4 | 59 | 84–96 | 156–8 |
| 7 | DMSO, 8.6 | Toluene | PTS, 1.24 | 2 | 45 | 80–90 | 155–8 |
| 8 | DMSO, 8.6 | Toluene | NaHSO$_4$, 1.5 | 2 | 56 | 85–97 | 152–7 |
| 9 | DMAc, 8.6 | Toluene | PTS, 1.24 | 2 | 73 | 90–95 | 153–8 |

NMP - N-Me pyrrolidone
DMAc - dimethylacetamide amount of toluene insoluble residue obtained on redilution of the ML was 0.04 g per gram of 3-Me-4,4'-DADPE-BMI produced.

EXAMPLE 13

Preparation of 3-Me-4,4'-DADPE-BMI

Example 12 was repeated as described above except for the use of 81 g of the diamine (0.38 mole) and the substitution of chlorobenzene for the toluene. Cyclization was complete within 2 hours at 112° C. (reduced pressure). With respect to the previous example, the yield on the first cycle increased to about 78%, but was no higher on the recycle runs. The m.p. range of products obtained was 156.7°–162.8° C.

While a number of examples illustrating particular embodiments of the present application have been given for the sake of illustration, it is understood that they are not limitative and that the invention may be carried out in different ways, with many modifications, variations and adaptations, without departing from its spirit or exceeding the scope of the appended claims.

We claim:

1. In a process for the preparation of substituted maleimides which comprises reacting the corresponding amines with maleic anhydride and effecting the thermal imidization of the resulting substituted amic-acids in a mixture of at least one non-polar and at least one polar aprotic solvent in the presence of an acidic catalyst, the improvement comprising selectively removing from the reaction mixture a substantial portion of the non-polar solvent, thus affording the precipitation of most of the final product.

2. A process according to claim 1, in which the portion of the non-polar solvent removed is between 50% to 90% and preferably between 60% and 80%.

3. A process according to claim 1 in which the maleic anhydride is used in an excess up to 60%, preferably 5% to 10%.

4. A process according to claim 1, which further comprises separating the precipitated product from the mother liquor and rediluting said mother liquor with an amount of said non-polar solvent, thus causing the precipitation of the impurities.

5. A process according to claim 4, which further comprises recycling the mother liquor, after removing the precipitated impurities.

6. A process according to claim 4, wherein the amount of non-polar solvent used for rediluting the mother liquor is comprised of between 0.5 and 1.5 parts by volume, and preferably between 0.7 and 1.3 parts by volume, of the mother liquor.

7. A process according to claim 5, wherein the mother liquor is recycled, at least prevalently, to the imidization stage of the process.

8. A process according to claim 1, wherein the total amount of solvents used is from 1.5 to 20 parts, and preferably from 2 to 9 parts, for each part of maleimide produced, and the ratio of non-polar to polar solvent is from 99% to 10% of the former to 1% to 90% by weight of the latter.

9. A process according to claim 8, wherein the polar solvent is in the amount of 5% to 20%, and preferably 10% to 15%, by weight of the solvent mixture.

10. A process according to claim 1, in which a part of the non-polar solvent which has been removed is used for amic-acid production.

11. A process according to claim 1, in which the reactions are performed in an inert, e.g. nitrogen, atmosphere.

12. A process according to claim 1, in which amic-acid formation is performed over a period of 0.1–10.0, preferably 0.25–1.0 hours.

13. A process according to claim 1, in which the imidization is carried out over a period of 0.5–72.0, preferably 1–4 hours.

14. A process according to claim 1, in which an non-polar solvent is used which boils at a temperature sufficiently below the boiling temperature of the polar solvent, so as to be readily separated from it by distillation.

15. A process according to claim 1, in which the reaction and/or concentration step is carried out under a vacuum.

16. A process according to claim 1, carried out in batch, semi-batch or continuous operation.

17. A process according to claim 1, wherein the amines employed are selected from the group consisting of m-phenylenediamine, aniline, toluidine, p-phenylenediamine, 4,4'-diaminodicyclohexylmethane, 1,4-diaminocyclohexane, 2,6-diaminopyridine, 4,4'-diaminodiphenylmethane, 2,2-bis (4-aminophenyl) propane, 4,4'-diaminodiphenyl ether, 4,4'-diamino-3-methyldiphenyl ether, 4,4'-diaminodiphenylsulfide,4,4'-diaminobenzophenone, 4,4'-diaminodiphenylsulfone, bis (4-aminophenyl) phenylamine, m-xylylenediamine, p-xylylenediamine, cyclohexylamine, 3-methyl-4,4'-diaminodiphenylmethane, 3,3'-diethyl-4,4'-diaminodiphenylmethane, 3,3'-dichloro-4,4'-diaminodiphenylmethane, 2,2',5,5'-tetrachloro-4,4'-diaminodiphenylmethane, 2,2-bis (3-methyl-4-aminophenyl) propane, 2,2-bis (3-ethyl-4-aminophenyl) propane, 2,2-bis (2,3-dichloro-4-aminophenyl) propane, bis (2,3-dimethyl-4-aminophenyl) phenylethane, ethylenediamine, hexamethylenediamine and xylidines, the non-polar solvents are selected from the group consisting of pure or mixed benzene, toluene, xylenes, ethylbenzene, diethylbenzene, octanes, methylcyclohexane, butylbenzenes, cumene, mesitylene, halogenated hydrocarbons including chlorobenzene, dichlorobenzenes, o-chlorotoluene, m-chlorotoluene, p-chlorotoluene, 1,2-dichloroethane, 1,2-dichloropropane, carbon tetrachloride, 1,1,1-trichloroethane, 1,1,2-trichloroethane, 1,1,1,2-tetrachloroethane, 1,1,2,2-tetrachloroethane, trichloroethylene, and tetrachloroethylene, and the aprotic polar solvents are selected from the group consisting of dimethyl sulfoxide, N,N-dimethylformamide, N,N-dimethylacetamide, hexamethylphosphoramide and N-methyl-2-pyrrolidone.

18. A process according to claim 1, wherein the imidization is carried out in the presence of one or more acidic catalyst(s) in an amount of from 0.001–1 mole, and preferably 0.1–0.4 mole per mole of amine.

19. A process according to claim 18, wherein the acidic catalyst comprises a long chain alkyl benzene sulfonic acid.

20. A process according to claim 18, wherein the acidic catalyst is selected from the group consisting of trifluoroacetic acid, an organic sulfonic acid, sulfuric acid, a sulfonated polymer, a sulfonated fluoropolymer, phosphoric acid, polyphosphoric acid, an organophosphoric acid and an acidic salt.

21. A process according to claim 20, wherein the organic sulfonic acid is selected from the group consisting of benzenesulfonic acid, p-toluenesulfonic acid, dodecylbenzenesulfonic acids, and trifluoromethanesulfonic acid.

22. A process according to claim 20, wherein the sulfonated polymer is a sulfonated polystyrene.

23. A process according to claim 20, wherein the organophosphoric acid is selected from the group consisting of mono- and diethylphosphoric acid.

24. A process according to claim 20, wherein the acidic salt is selected from the group consisting of sodium- and ammonium hydrogen sulfate.

* * * * *